United States Patent [19]

O'Brien et al.

[11] Patent Number: 5,521,278

[45] Date of Patent: May 28, 1996

[54] INTEGRATED PROCESS FOR THE MANUFACTURE OF LACTIDE

[75] Inventors: William G. O'Brien, Newark, Del.; Lisa A. Cariello, Springfield; Theodore F. Wells, Downingtown, both of Pa.

[73] Assignee: Ecological Chemical Products, Wilmington, Del.

[21] Appl. No.: 292,756

[22] Filed: Aug. 18, 1994

[51] Int. Cl.$^6$ .............................. C08G 63/08; C08F 6/00
[52] U.S. Cl. .................... 528/354; 528/480; 528/481; 528/484; 528/485; 528/357; 528/361
[58] Field of Search .................... 528/480, 481, 528/484, 485, 354, 357, 361

[56] References Cited

U.S. PATENT DOCUMENTS

| | | | |
|---|---|---|---|
| 3,621,664 | 11/1971 | Saxer | 549/274 |
| 4,835,293 | 5/1989 | Bhatia | 549/274 |
| 5,023,349 | 6/1991 | Bhatia | 549/274 |
| 5,023,350 | 6/1991 | Bhatia | 549/274 |
| 5,043,458 | 8/1991 | Bhatia | 549/274 |
| 5,089,632 | 2/1992 | Paul | 549/274 |
| 5,091,544 | 2/1992 | Bhatia | 549/274 |
| 5,136,057 | 8/1992 | Bhatia | 549/274 |
| 5,138,074 | 8/1992 | Bellis et al. | 549/274 |
| 5,142,023 | 8/1992 | Gruber et al. | 528/354 |
| 5,196,581 | 3/1993 | Morse et al. | 564/8 |
| 5,208,297 | 5/1993 | Ford et al. | 525/415 |
| 5,223,630 | 6/1993 | Lin | 549/274 |
| 5,229,528 | 7/1993 | Brake et al. | 549/274 |
| 5,236,560 | 8/1993 | Drysdale et al. | 203/99 |
| 5,247,058 | 9/1993 | Gruber et al. | 528/354 |
| 5,247,059 | 9/1993 | Gruber et al. | 528/354 |
| 5,258,488 | 11/1993 | Gruber et al. | 528/354 |
| 5,264,614 | 11/1993 | Brake | 560/179 |
| 5,264,626 | 11/1993 | Brake et al. | 562/589 |
| 5,288,881 | 2/1994 | Drysdale et al. | 549/274 |
| 5,310,599 | 5/1994 | Ford | 528/354 |
| 5,326,887 | 7/1994 | Di Cosimo et al. | 549/274 |

OTHER PUBLICATIONS

Carrothers, et al, "Studies of Polymerization and Ring Formation. X. The Reversible Polymerization of Six–Membered Cyclic Esters", *American Chemical*, 54, 761–772.
British Polymer Journal, vol. 23, No. 3, pp. 235–240 (199).
"High–Molecular, Particularly Optically Active Polyesters of Lactic Acid, A Contribution to the Stereochemistry of Macromolecular Compounds", *Makromol. Chem.* 30, No. 1:23–38, Apr. 1959.

*Primary Examiner*—Shelley A. Dodson

[57] ABSTRACT

An integrated process for the manufacture of lactide from a solution of lactic acid in de-ionized water comprising the sequential steps:

A. Dehydrating the aqueous lactic acid in at least two stages to effect condensation polymerization of the lactic acid and the formation of oligomers in which the average number of monomer units is 8–25, the dehydration stages being conducted in equipment fabricated from low ferrous materials;

B. Thermally cracking the oligomers in the presence of depolymerization catalyst to form lactide vapor of which the average residence time within the cracking zone is less than 15 seconds;

C. Condensing the lactide vapor and fractionally distilling the condensate to remove concentrated lactide as a liquid sidestream; and D. Subjecting the concentrated lactide sidestream to melt crystallization to separate purified lactide having an Acidity Potential less than 6.

23 Claims, 10 Drawing Sheets

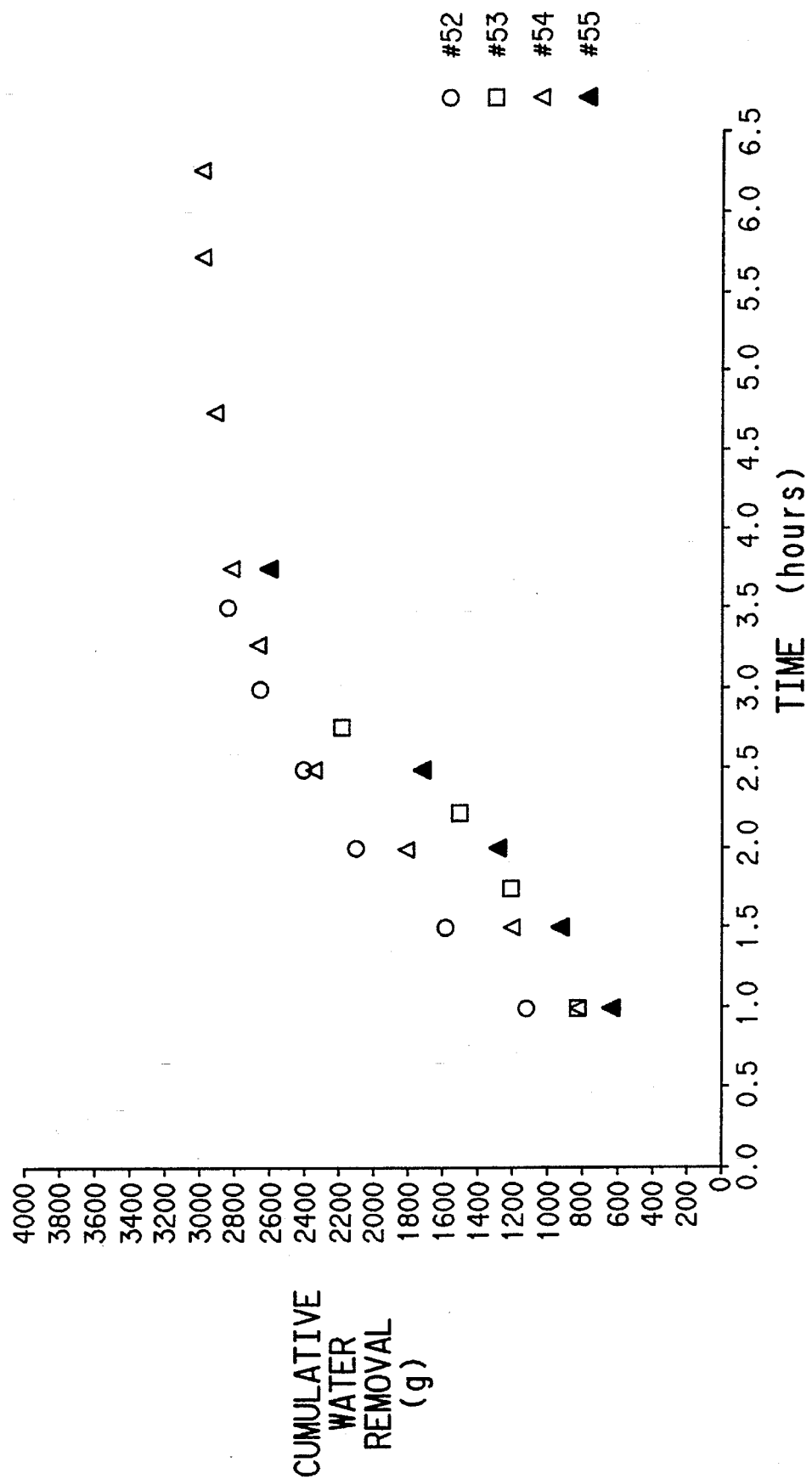

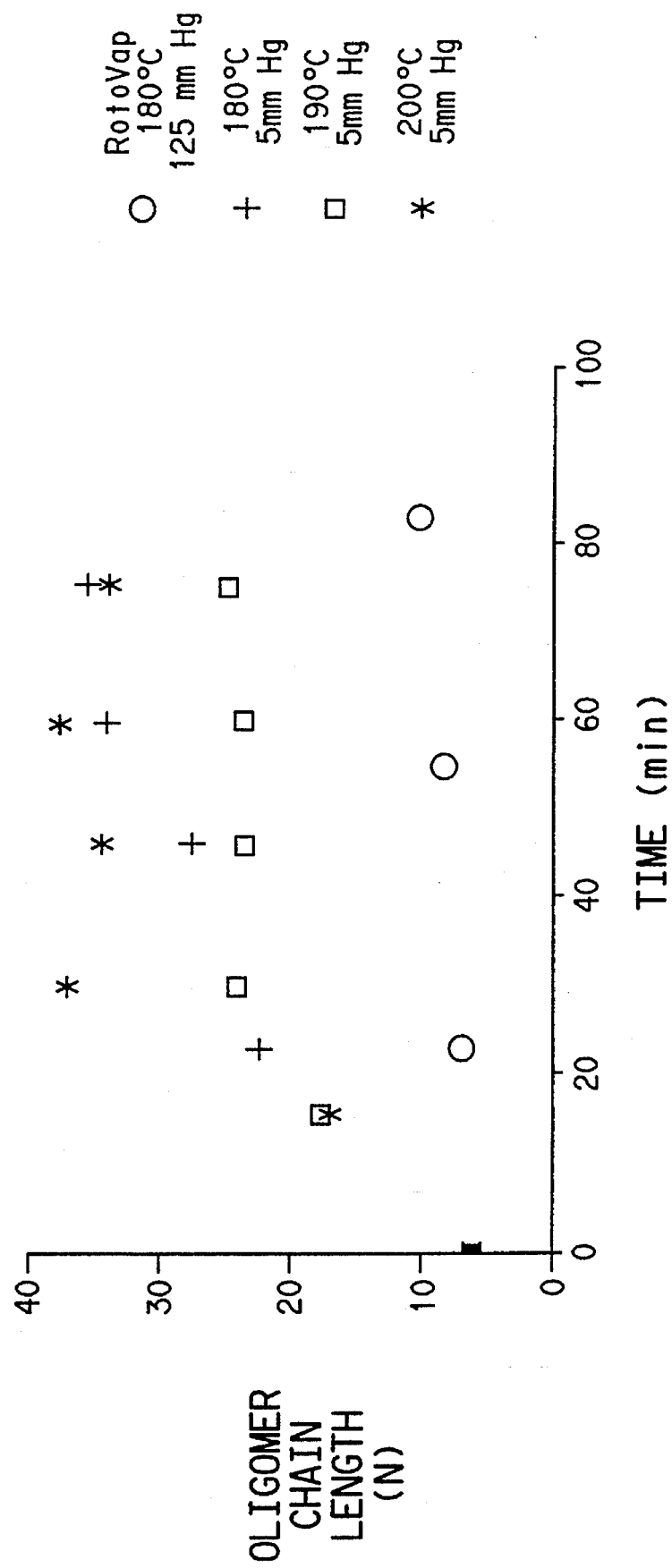

INTEGRATED PROCESS FOR THE MANUFACTURE OF LACTIDE

FIELD OF THE INVENTION

The invention is directed to an integrated process for the manufacture of purified lactide. In particular, the invention is directed to such process in which high purity lactide is produced efficiently with high yields.

BACKGROUND OF THE INVENTION

Because of its biodegradability, polylactide [poly(lactic acid)] has become of increasing commercial interest as a substitute for less readily degradable materials such as polyolefins and polyurethanes. The basic technology for making polylactide extends back to as early as 1932 with the work of Carrothers et al. ["Studies of Polymerization and Ring Formation. X. The Reversible Polymerization of Six-Membered Cyclic Esters", American Chemical Society Journal, v. 54, pp 761–772]. Nevertheless, the commercial acceptance of polylactide has been inhibited by the high cost of such polymers as compared to polyolefins and polyurethanes. However, as concerns for the environment become greater, the urgency of using more environmentally friendly materials such as polylactide has become correspondingly greater. To meet this urgency, there exists a substantial need for more economical ways of making poly(lactic acid) [PLA].

The basic process for making PLA involves the dehydration of aqueous lactic acid to form a mixture of oligomers of lactic acid. The oligomers are then subjected to thermocracking to make lactide, that is, the cyclic diester of lactic acid. The lactide is admixed with a ring-opening catalyst and subjected to heat and/or pressure to form PLA.

This general method for making PLA is illustrated by the integrated process disclosed in U.S. Pat. No. 5,142,023 to Gruber et al. and related patents U.S. Pat. No. 5,247,058, U.S. Pat. No. 5,247,059 and U.S. Pat. No. 5,258,488.

Gruber et al. disclose an integrated process for making PLA from aqueous crude lactic acid comprising the following sequential steps:

1. In two stages, evaporating water from the crude lactic acid to form lactic acid oligomers having a molecular weight of 100–5,000 (n=1.1– 72);

2. Mixing the oligomers with depolymerization catalyst and thermally cracking the oligomer to form lactide vapor;

3. Removing lactide vapor from the thermal cracking zone, condensing it and fractionally distilling the lactide condensate to form a "purified" lactide; and 4. Reacting the "purified" lactide to form PLA.

It is recognized by those skilled in the art that water and/or its reaction products with materials such as lactic acid and lactic acid oligomers should be kept at very low concentrations in order that high molecular weight polymers can be made therefrom. For example, see *British Polymer Journal*, Vol. 23, No. 3, p. 235–240 (1990), which teaches that the content of free carboxylic groups should not exceed 0.8 meq/g (800 meq/kg). Nevertheless, it has been found that even such modest amounts of acids are much too high for the manufacture of high purity lactic acid polymers.

However, the Gruber et al. process is based on the premise that the lactide from the oligomer cracking unit, if fractionated by distillation, will be suitable for polymerization without further treatment such as crystallization or solvent extraction, both of which have been suggested for this use in the prior art. However, it has been found that the process taught by Gruber et al. has several shortcomings which make it unsuitable for the manufacture of high quality PLA.

In particular, following the teaching of the Gruber process results in (1) a manufacturing sequence which requires extensive time for polymerization, (2) excessive equipment costs and (3) products therefrom having inadequate properties for many applications. Many of these polymer quality concerns arise from the fact that the process as taught fails to recognize the cause and effect of the many and varied side reactions which adversely affect polymer quality.

While the Gruber et al. process purports to advance the technology of making PLA, it nevertheless falls considerably short of teaching a practical process which can make PLA readily available in commercial quantities with the high quality that is needed for the widespread use of PLA in consumer applications. Therefore, there remains a substantial unmet need for a practical route for making high quality lactide which is suitable for making PLA by ring-opening polymerization thereof.

SUMMARY OF THE INVENTION

In its primary aspect, the invention is therefore directed to an integrated process or the manufacture of purified lactide from an aqueous solution containing at least 50% wt. lactic acid comprising the sequential steps:

A. Feeding a solution of crude lactic acid in de-ionized water to a first heated zone in which free water is removed by evaporation and a molten mass of condensation polymer containing lactic acid and a minor amount of free water is formed by condensation polymerization to an extent that the average number of monomer units (n) in the condensation polymer is 2–8;

B. Feeding the molten mass of condensation polymer from step A to at least one further heated zone in which the diffusive surface area of the polymer is increased, the residual lactic acid and condensation polymer are further condensation-polymerized to an extent that n is 8–25 and both free water and bound water are removed by evaporation, steps A and B being carried out within equipment the surfaces of which in contact with the reactants are fabricated from low ferrous materials;

C. Contacting the molten condensation polymer with an alkali metal-free depolymerization catalyst in a cracking zone operated at a liquid temperature no higher than 240° C. and pressure sufficient to effect cracking of the molten condensation polymer with the concomitant formation of (1) a vaporous reaction mixture containing water, lactic acid, lactide and entrained heavy oligomers and (2) molten liquid heavy ends containing heavy oligomers;

D. Removing the vaporous reaction mixture from the cracking zone at a rate such that the average residence time of the lactide vapor within the cracking zone is less than 15 seconds;

E. Condensing the vaporous reaction mixture and fractionating the condensate therefrom whereby lactic acid, water and minor amounts of lactide are removed as vapor overhead, concentrated lactide is removed as a liquid side stream and the heavy ends are removed as molten liquid; and F. Subjecting the concentrated lactide to melt crystallization by which a purified lactide fraction having an Acidity Potential less than 6 meq/kg of lactide is separated from a residual lactide fraction having an Acidity Potential of at least 30 meq/kg.

In a second aspect, the invention is directed to a method of making a concentrated stream of lactide from lactic acid oligomers comprising the sequential steps:

A. Contacting molten lactic acid oligomers in which the average number of monomer units is 8–25 with an alkali metal-free depolymerization catalyst in a cracking zone operated at a temperature no higher than 240° C. and pressure sufficient to effect cracking of the molten oligomers with the concomitant formation of (1) a vaporous reaction mixture containing water, lactic acid, lactide and entrained heavy oligomers and (2) molten cracker bottoms containing heavy oligomers;

B. Removing the vaporous reaction mixture from the cracking zone at a rate such that the average residence time of the lactide vapor within the cracking zone is less than 15 seconds;

C. Condensing the vaporous reaction mixture and fractionating the condensate therefrom whereby lactic acid, water and minor amounts of lactide are removed as vapor overhead, concentrated lactide is removed as a liquid side stream and the condensate heavy ends are removed as molten liquid;

D. Cooling the molten liquid cracker bottoms to around 190° C. and removing them from the cracking zone at a rate such that the average residence time of the molten cracker bottoms in the cracking zone is less than 15 minutes; and E. Subjecting the cooled molten liquid cracker bottoms to dehydration or to hydrolysis followed by dehydration and recycling the resultant dehydrate to the cracking zone.

BRIEF DESCRIPTION OF THE DRAWING

The Drawing consists of four figures as follows:

FIG. 4 is a graphical correlation of the effect of alkali metal on racemization.

DEFINITIONS

Figure 1A:
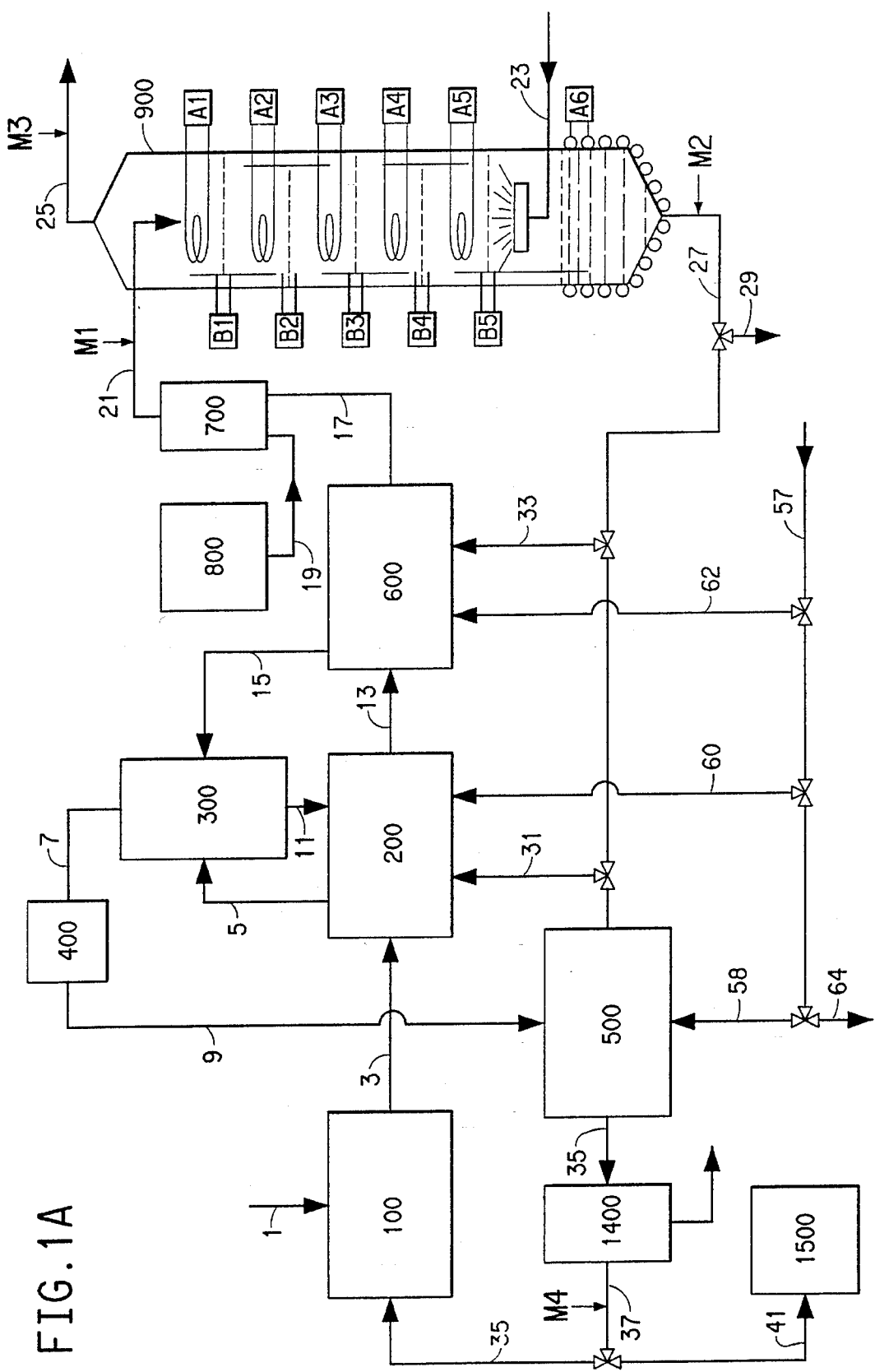
FIGS. 1a and 1b together constitute a schematic flow diagram of a preferred manner of carrying out the process of the invention.

A. "Acidity Potential," when used with respect to a given process stream, refers to the content therein of acidic compounds or potential acid-forming materials such as water. Such materials are measured asmeq/kg of material;

B. "Alkali metal-free" is used with reference to depolymerization catalysts and denotes that such materials contain no more than 10 ppm by weight alkali metal or alkaline earth metal, basis lactide;

C. "Bound water" means water formed by the condensation reaction of two or more organic compounds containing a plurality of hydroxyl (—OH) groups, for example, water produced by the oligomerization of lactic acid;

D. "De-ionized Water" means water which contains no more than 100 ppm by weight ions of alkali metals or alkaline earth metals;

E. "Free water" means water physically associated with a body of reactants, e.g., as a solvent or as water of crystallization;

F. "Heavy oligomers" means those oligomers of lactic acid formed by condensation polymerization of 3 or more lactic acid molecules; and G. "Non-ferrous" refers to the iron content of materials of construction. In particular, non-ferrous materials are those which contain less than 50% by weight iron or iron ions. Iron content is of concern in the process of the invention where it comes into contact with reactants, particularly acidic and/or aqueous reactants.

DETAILED DESCRIPTION OF THE INVENTION

A. In General

The polymerization and copolymerization of aliphatic hydroxy carboxylic acids such as lactic acid are usually carried out by ring-opening polymerization of their corresponding cyclic esters in the presence of a ring-opening catalyst such as divalent tin. Thus, as mentioned hereinabove, a conventional method for making poly(lactic acid) [polylactide] involves the dehydration of aqueous solutions of lactic acid to form oligomers of the lactic acid, which are then thermally cracked to form the cyclic diester (lactide) of lactic acid. The lactide is then mixed with a ring-opening catalyst and subjected to heat and/or pressure to effect ring opening of the cyclic diester and formation of polylactide. (As used herein, the terms "polylactide," "poly(lactic acid)" and "PLA" are interchangeable.)

In polymerizing lactide, it has been found that the presence of even small amounts of acid and acid precursors, such as lactic acid, inhibits ring-opening of the lactide and increases the amount of contaminants in the polymer. Thus, polymerization time becomes excessive if high conversion levels are sought. The process of the invention is therefore directed to producing lactide which has low Acidity Potential and reduced contamination by products from thermal degradation.

B. Lactic Acid

The aqueous lactic acid which can be used in the process of the invention can be made synthetically or by biochemical means such as the fermentation of various sugar sources such as whey permeate, corn glycose, beet sugars and the like. It is, however, preferred that the lactic acid feed materials contain no more than about 50% by weight water. Even less water content is preferred since less energy must be expended to remove such smaller amounts of water.

Lactic acid, of course, exists in two forms which are optical enantiomers, i.e., D-lactic and L-lactic acids. Either of these lactic acid forms can be polymerized to form oligomers and thus can be used in the invention to make lactides. The lactides produced therefrom have three types of optical activity depending on the composition of the crude lactic acid. If the feed contains only L-lactic acid, the resulting product is L-lactide. If the feed contains only D-lactic acid, the resulting product is D-lactide. But if the feed contains a mixture of D- and L-lactic acid, the resultant lactide is an L, D and meso-lactide mixture. The process of the invention can utilize either form of lactic acid as primary feed. However, it will usually be preferred that either the L- or D-lactic acid be used in substantially pure form with respect to optical purity.

Despite their purity, the optical activity of lactic acid and lactides made therefrom tends to change under certain conditions toward optical inactivity in which equal amounts of the D- and L-enantiomers are present. This tendency is aggravated by impurities and by exposure to high temperatures for long periods of time (thermal exposure). Furthermore, the rate of racemization is affected by the relative concentrations of D- and L-enantiomers. The invention process is therefore oriented toward the minimization of those operating variables which adversely affect optical purity.

C. Oligomer Formation by Dehydration

For the purposes of the invention, it is essential that the dehydration of lactic acid to form oligomers be conducted in such manner that entire dehydration step is carried out at the lowest possible temperature consistent with obtaining economical yields of oligomer which has appropriate optical purity.

Furthermore, to avoid racemization and other side reactions which arise from the presence of alkali and alkaline earth metals, it is preferred that the water in which the lactic acid is dispersed contain no more than 100 ppm by weight of such metal ions and preferably still no more than 50 ppm.

It is, of course, well known that water reacts with lactic acid oligomers to reduce their chain length. Therefore, it is essential to remove as much water from the lactic acid as is practically possible in order to obtain oligomers having high enough molecular weight. In this regard, it is known that if the feed acid is comprised of, say, 98% L-lactic acid, then the oligomers and ultimately the lactide can contain no less than 3.9% meso-lactide. Furthermore, depending upon the time-temperature encountered during dehydration and the nature of the particular depolymerization, the optical purity of the resultant lactide will be reduced even further. Therefore, the dehydration step of the invention is directed to removing as much water as is possible while at the same time minimizing those factors which adversely affect optical purity.

From the standpoint solely of water removal rate, it would be desirable to operate at a temperature substantially above the boiling point of water. However, if the temperature of dehydration is raised too high, excessive racemization of the formed oligomers takes place. The degree to which this is a problem in the dehydrator depends on the amount of racemization which can be tolerated in the feed to the depolymerization unit. However, it has been found that 240° C. is a practical maximum temperature above which the degree of thermal racemization becomes excessive for most applications. A temperature of no more than 180° C. is further preferred. To be able to utilize lower temperatures and thereby keep racemization of the oligomers to a low value, it is preferred to operate the dehydrators, especially the second stage, at reduced pressure.

The preferred operating conditions for dehydration are determined by balancing two factors: (1) at lower values of n, more water remains in the system and lactide yield in the cracking step is reduced; and (2) at higher values of n, there is less water in the system, lactide yield is higher, but quality is poorer.

In the dehydration phase of the invention, the first dehydration stage is operated in such manner that substantially only free water is removed from the lactic acid feed and the average number of molecules in the product therefrom is no more than 8 and preferably only 4–6. It is feasible to speed up water removal in the first stage by using a vacuum; however, it is not so critical as in the subsequent stage(s). Reduced pressure operation can, however, be used throughout all stages of the dehydration process. The first stage of dehydration can readily be carried out in a packed column.

It is definitely preferred to operate subsequent dehydration stages at a vacuum in order successfully to remove the relatively small amounts of free water and bound water in the lactic acid within the least practicable time and at the lowest practicable temperature. Again, depending on the nature of the depolymerization catalyst which will be used in later processing and in the amount of thermal racemization which can be tolerated in the lactide product, it will be preferred to operate the second dehydration stage and any subsequent dehydration stages at a substantial vacuum.

In general, it is preferred that the dehydration phase of the invention be carried out in at least two stages. In the first stage, essentially only free water is removed and the average number of monomer units (n) in the product therefrom is 4–6 and preferably n is no higher than 8.

In the subsequent dehydration stage(s), the lactic acid is further oligomerized by removal of bound water until the average number of lactic acid molecules in the oligomeric mixture (n) is 8–25. Because of the high viscosity of oligomers in which n exceeds about 25, the rate of diffusion of bound water from the condensation reactions becomes limiting and makes the production of higher molecular weight oligomers even more difficult. That is, water removal becomes diffusion limited. Therefore, it is preferred that the oligomeric mixture in subsequent dehydration stages be carried out in such manner that the surface area of the mixture is enhanced. Such enhanced surface area can be achieved, for example, by the use of wiped-film equipment or by the use of high pressure spraying devices. By these means, the rate of diffusion is raised and the overall time-temperature exposure of the oligomer is kept to a minimum. It is preferred in the practice of the invention that n not exceed 25 since the viscosity of higher molecular weight oligomers becomes so high that admixing the depolymerization catalyst without subjecting the oligomers to very high temperatures becomes difficult.

Two stage dehydration will ordinarily be carried out so that n of the first product is 2–8 (preferably 4–6) and n of the second stage is 8–25. With three stage operation, n of the first stage product would preferably be 2. Product from the second stage product would have n=ca. 10 and product from the last stage would have n=15–25.

D. Thermal Decomposition Catalyst

It is preferred in the process of the invention that the thermal decomposition of the lactic acid oligomers be facilitated by the addition of a depolymerization catalyst. Such catalysts include metal oxides, hydroxides, carbonates and carboxylates of $Sn^{II}$, $Sn^{IV}$, $Sb^{III}$, $Zn^{II}$ and $Bi^{III}$. Examples of such catalysts include tin octoate (tin 2-ethylhexoate), tin lactate, tin oxide, antimony octoate, bismuth octoate, zinc stearate, zinc octoate and the like. (In many instances, such depolymerization catalysts can also function as a ring-opening catalyst for polymerization of the lactide.) Either solid or soluble catalysts can be used and the catalyst can be dispersed in the oligomer feed to the depolymerization unit or the oligomers can be contacted with a fixed bed of such catalyst within the thermocracking vessel. When the catalyst is dispersed in the oligomer cracking feed, it is preferred that the catalyst be used in amounts of 0.05–6% by weight, and preferably 0.5–2.0% by weight.

It will be recognized that the use of a suitable depolymerization catalyst enables the thermocracking operation to be operated at milder conditions of temperature. The use of milder temperature conditions, of course, reduces the amount of lactide decomposition caused by time-temperature exposure.

Though the precise composition of the catalyst is not critical, i.e., a wide variety of depolymerization catalysts can be used, it is nevertheless quite important that the catalyst be substantially free of alkali metal and alkaline earth metal ions. It is known that alkaline substances have the adverse effect of causing racemization. ("High-Molecular, Particularly Optically Active Polyesters of Lactic Acid, A Contribution to the Stereochemistry of Macromolecular Compounds", *Makromol. Chem.* 30, no. 1:23–38, April, 1959). However, applicants have found that limiting the amount of alkali metal and alkaline earth metal ions in the reaction system, in combination with the use of non-ferrous materials of construction, greatly reduces the effect of other side reactions which degrade both the quality and yields of the lactide.

Experience with such catalysts has shown that no single catalyst is superior from the standpoints of both quality and depolymerization rate. However, from the standpoint of depolymerization rate, a preferred catalyst is antimony octoate. From the standpoint of optical quality, a preferred catalyst is tin lactate. Nevertheless, whatever catalytic metal may be used, it is preferred that it be present in its stable valence state lest oxidation of the catalyst cause formation of color formers and other contaminants in the lactide product.

E. Lactide Formation by Thermocracking

As outlined hereinabove, formation of lactide is accomplished by thermally cracking the oligomers (n=8–25) in the presence of a suitable catalyst. This can be done by passing the heated oligomer through a fixed bed of catalyst within the cracking unit or it can be done by admixing the catalyst with the oligomer feed to the cracking unit. In the latter case, in order to minimize the time-temperature exposure of the oligomers within the cracker, it is preferred that the catalyst be preheated and mixed with the oligomer feed. The oligomer is then heated quickly as it passes into the upper end of the thermal cracking vessel to the topmost of a series of trays, each having liquid downcomers to the next lower tray. The liquid oligomer is heated to its cracking temperature as it passes down through the series of trays and the lactide cracking product becomes vaporized and is removed from the vessel overhead. To assist the separation of lactide and other vaporized materials from unreacted heavy oligomers and other residual liquid materials, a stream of heated dry nitrogen gas is passed upward through the column countercurrently to the falling oligomer liquid. The nitrogen stream in combination with the rising lactide vapor effects more efficient stripping of the vapor from the liquid in the cracking vessel. The use of nitrogen-assisted stripping in this manner is disclosed in U.S. Pat. No. 5,023,349 and U.S. Pat. No. 5,091,544 to Bhatia.

Suitable temperatures for the depolymerization vary widely, but will usually be within the range of 185°–270° C. and preferably 200°–220° C. The optimum temperature for any particular oligomer feedstock will vary with the composition of the feedstock, the catalyst and the pressure within the cracker. The pressure within the cracking unit can vary widely and thus can be either above or below atmospheric pressure. In some instances, it is desirable to operate at reduced pressure in order to lower the time-temperature exposure of the vaporized lactide product. Operating efficiency of the lactide recovery operation can be raised if the oligomer cracker is also operated under vacuum with reduced amounts of nitrogen for stripping.

Though the precise reactor configuration is not critical, a particularly preferred design is a columnar reaction vessel having a vapor product outlet at the top of the column, an oligomer feed line near the top of the column and a series of distillation trays proceeding downward, each having liquid downcomers to the next lower tray. Heavy liquid oligomers which have not been converted flow downward from the lowest tray and are collected and removed from the bottom of the column. Nitrogen gas for stripping is introduced between the liquid bottoms and the lowest tray and is directed upward into the downcoming flow of unconverted oligomer. Sieve plate distillation trays, each bearing a liquid layer of unconverted oligomer, have been found to be very effective to mix the feed, vapor and liquid intimately and thus to improve reaction efficiency.

In a preferred mode of operating the cracking function, solid inert packing is added onto the top of each of the sieve plate distillation trays by which the reaction efficiency of the column is considerably improved. In particular, the addition of packing to the sieve plates within the thermal cracking vessel adds greatly to the reaction efficiency of the thermal cracking operation, as follows:

1. The packing improves the heat transfer efficiency between the vapor and liquid;
2. An increased number of theoretical reaction stages is realized;
3. There is more intimate contact between the nitrogen and the downcoming liquid, therefore, there is more effective stripping; and
4. For a given liquid height on the trays, the amount of liquid is reduced, thus reducing the average residence time of the reactants and also reducing the degree of racemization.

Suitable packing materials are conventional column packing such as Berl saddles, Raschig rings, plain rings, spheres and the like. Such packing must, however, be made from materials which are chemically inert with respect to the reactants.

Alternatively, instead of using a series of distillation trays, an intermediate zone in the column can be packed with a solid foraminous bed of catalyst through which the oligomer feed is passed downward. Such catalyst bed would contain a series of heating coils to effect heating of the oligomers to their cracking temperature before emerging from the catalyst bed.

Regardless of the reactor configuration, it is important that the average residence time of the vapor lactide product within the reactor be kept to a minimum in order to avoid undesirable side reactions. Therefore, it is preferred that the average residence time of vapor within the reactor be no more than 15 seconds and preferably no more than 10 seconds. Similarly, it is preferred that the average residence time of the unreacted oligomers within the reactor be no more than 45 minutes and preferably no more than 25 minutes in order to minimize the production of highly viscous residues which are not readily pumpable.

The bottoms product from the cracking unit consists mainly of heavy oligomers, crosslinked species, spent catalyst and small amounts of absorbed volatiles, and color bodies. It is therefore preferred that the cracker bottoms be removed from cracking zone, heated and subjected to vacuum flashing to remove the small amounts of volatiles therefrom. A portion of the bottoms can be recycled to hydrolysis or to dehydration. However, some will likely need to be removed from the process to prevent excessive buildup of inert spent catalyst.

F. Lactide Recovery

The vapor overhead stream from the oligomer cracker contains substantial quantities of lactide. However, the stream also contains substantial quantities of impurities such as water, light decomposition products and entrained liquids such as oligomers and other heavy ends, which must, of course, be separated from the lactide. In the process of the invention, this is preferably done in a two-stage operation which involves condensing the cracker overhead to separate the more volatile materials and then fractionally distilling the lactide-enriched condensate. The overhead from the distillation column consists mainly of lactic acid, water, nitrogen and entrained oligomers and lactide. A liquid stream containing principally lactide is withdrawn from the side of the column below the feed tray and heavy ends, consisting mainly of heavy oligomers, are collected and removed from the bottom of the column. The lactide recovery is carried out under vacuum in order to keep the temperature low. In operation of the cracker overhead condenser, it is important to optimize the temperature. That is, the temperature should be high enough to removed a maximum amount of water, but low enough to maximize lactide recovery.

Heavy ends from the lactide distillation can be recycled to the lactide vacuum distillation column or they can be recycled to one of the dehydration stages.

G. Lactide Purification

In order to purify the concentrated lactide from the lactide recovery step, it is preferred to subject the concentrated impure lactide therefrom to melt crystallization by which the lactide can be freed from impurities such as lactic acid, oligomeric residues, solvents and catalyst. This method of purification can be comprised of one or more stages which involve the following steps:

1. Cooling molten concentrated lactide at least to the freezing point of the lactide, thus partially crystallizing the melt and forming a solid crystalline phase having lower impurity content and a liquid phase having a higher impurity content; and 2. Separating the crystalline phase from the more impure liquid phase; and 3. Optionally subjecting the separated crystalline phase to "sweating" whereby it is warmed to a temperature below the lactide melting point to melt selectively a portion of the remaining impurities and a minor amount of the lactide.

The impure liquid from the melt crystallization process can be recycled for further separation of residual lactide.

Various types of equipment are known for melt crystallization. For example, a simple batch method involves the use of a tank with multiple heat transfer elements equipped for heating and cooling at a controlled rate or with a controlled temperature differential with respect to the material in the tank. The product to be purified is simply melted, frozen, drained, sweated, re-drained and the purified product is melted. The equipment is easily instrumented for automatic control. A preferred semi-continuous method involves the use of vertical cooling tubes and a method for pumping the melted crude material to the top of the tubes and draining the liquid impurities from the bottom of the tubes. The method may be made fully continuous by using a number of the tube assemblies with various timing or control devices. A preferred type of apparatus for this function is disclosed in U.S. Pat. No. 3,621,664 and U.S. Pat. No. RE 32,241. Using such apparatuses, the melt crystallization process can be carried out in either parallel or in series according to the purity, yield and economic criteria of the lactide product.

The use of melt crystallization processes for the purification of impure lactide is disclosed in copending U.S. Pat. No. patent application Ser. No. 08/231,964, filed on Apr. 22, 1994, by O'Brien et al.

H. Ring-opening Catalyst and Polymerization

The purified lactide product made by the process of this invention can be ring-opening polymerized by a wide variety of metal-containing catalysts, many of which are well know in the art. In particular metal oxides, carbonates and carboxylates of $Sn^{II}$, $Sb^{III}$, $Zn^{II}$ and $Bi^{III}$ are all effective to a substantial degree. However, preferred catalysts are compounds of trivalent lanthanum and rare earth metal compounds such as those disclosed in Ford et al., U.S. Pat. No. 5,208,297. Suitable catalysts include tin octoate (2-ethylhexoate), tin lactate, tin oxide, antimony octoate, bismuth octoate, zinc stearate, zinc octoate, lanthanum bis(2,3,6,6-tetramethyl-heptane-3,5-dionato) i-propoxide and the like.

The monomer-to-catalyst ratio (molar basis) is generally maintained below 20,000, but usually not less than 500. Good results have been observed when the monomer/catalyst ratio is within the range of 15,000 to 1,000, with the preferred ratio being from 10,000 to 4,000. By employing a monomer/catalyst ratio of 1000 and maintaining a low Acidity Potential, very high conversions can be achieved in as little as 2 minutes. However, when monomer to catalyst ratios of 500 or less are used, the resultant polymer is frequently discolored, contains contaminants and is unstable.

Lactide polymerization is generally carried out with both elevated temperature and pressure in order to reduce the time required for getting high polymer conversion. For example, the polymerization can be carried out in one or more stages at a temperature of 120°–220° C. and a pressure which may be as high as several thousand pounds per square inch. In any event, it is preferred that the polymerization be carried out as rapidly as possible to reduce thermal degradation of the polymer. The purified lactide of the invention is particularly advantageous in view of its very low Acidity Potential which enables a high degree of polymerization to be carried out in as little as two minutes. This compares to usual polymerization times of two or more hours as are disclosed in the above-referred Gruber patent. It is preferred that the Acidity Potential of the lactide from the process of the invention be no higher than 6. Even faster polymerization rates can be obtained if the Acidity Potential is lower, e.g., an Acidity Potential of 2 or less is still further preferred. (See U.S. Pat. No. 5,310,599 to Ford. )

The polymerization can be carried out in any standard equipment. Continuous polymerization can be effected in a screw extruder, or in a reactor vessel having good mixing capability so that a homogeneous polymer product can be obtained. For example, a stirred tank can be used for either batch or continuous polymerization.

Lactide polymerization can be carried out either with or without a solvent. It is, however, preferred to employ bulk polymerization, that is, polymerization without solvent. A particularly good way of doing this is to carry out partial polymerization in a stirred tank reactor and then complete the conversion in a screw extruder. The polymerization catalyst can be added to the lactide before and/or during polymerization.

A preferred method for carrying out the invention is illustrated by reference to the Drawing as follows:

With reference to FIG. 1a, crude lactic acid is fed via feed line 1 to mixing vessel 100 in which the fresh feed is mixed with various recycle streams from later processing steps and the admixture is pre-heated to a temperature below which any substantial evaporation of water takes place. The heated admixture of crude lactic acid and recycle streams is pumped via line 3 to a first dehydrator stage 200 in which the mixture is heated further to evaporate free water from the feed and to begin condensation polymerization of the lactic acid to an extent that the average number of monomer units in the admixture is from 2 to 4.

Free water and water from the condensation polymerization are vaporized overhead. The predominantly aqueous overhead contains small amounts of entrained liquid lactic acid and is passed via vapor removal line 5 to separator 300 in which the water and entrained lactic acid are separated. The separated water vapor is passed via line 7 to condenser 400 in which the water is condensed and then pumped through line 9 to hydrolysis unit 500. The separated lactic acid is then returned to dehydrator 200 via line 11. The aqueous solution of condensation polymer in dehydrator 200 is optionally admixed with various recycle streams from later steps of the process.

The condensation polymer product from dehydrator 200, in which the average number of monomer units is 2–8, is passed via line 13 to second stage dehydrator 600. The feed is then heated further to effect water removal and condensation polymerization to a level such that the average number of monomer units is 8–25. It is preferred that the second stage dehydrator be operated at a reduced pressure not lower than about 10 mm Hg in order to permit effective water removal at a lower temperature.

The water vapor from second stage dehydrator 600, which contains very small amounts of entrained lactic acid, is removed overhead and passed via line 15 to separator 300 in which the separated water and lactic acid are disposed of in the manner described above with respect to the first dehydrator stage overhead. The condensation polymer from the second stage dehydrator 600 is also optionally admixed with various recycle streams from later steps of the process.

The condensation polymer (oligomers) from the second dehydrator stage is passed via line 17 to pre-heater 700 in which it is admixed with liquid depolymerization catalyst which has been provided via line 19 from catalyst supply tank 800. The admixture of catalyst and oligomer is heated to about 215° C. and passed via line 21 into the upper end of cracking vessel 900 onto the topmost of a series of 5 perforated fractionation trays extending down the vessel, each having liquid downcomers connecting to the next lower tray in the series.

It is noted that the surfaces of the process lines both to and from the dehydrator vessels 200 and 600, which come into contact with the lactic acid feed and condensation polymer, are constructed of low ferrous metals in order to avoid the formation of corrosion products which might later cause discoloration of lactide product and also to reduce side reactions which would adversely affect the purity of the product from the process of the invention.

Within the cracking vessel 900, thermally induced depolymerization (cracking) of the oligomer to form cyclic diester takes place and the reaction mixture therefrom is fractionated. Each of the trays is equipped with heating coils (A1–A5) which provide heat of reaction to the feed and enable the temperature of liquid on the trays to be controlled. In particular, by providing heat for the thermal cracking reaction within the cracking unit instead of preheating the oligomer feed, the time-temperature exposure of the feed and product is minimized, undesirable side reactions are lessened and the yield of lactide from the cracking unit is thereby maximized. By controlling the heat input to each tray and by adding more heat to the lower trays, the desired degree of cracking can be controlled throughout the cracking vessel.

A stream of heated nitrogen gas is introduced into the cracking unit 900 below the lowermost fractionation tray via line 23 to effect thorough stripping of the downcoming liquid. The vapor overhead, containing nitrogen gas, water, lactic acid and lactide vapors and small amounts of entrained heavy oligomers, is removed overhead through line 25 at a rate such that the average residence time of the lactide vapor within the high temperature environment of the cracking unit is less than about 15 seconds and preferably no more than 10 seconds.

Each of the fractionation trays in the cracking unit 900 is equipped with a sensing device B1–B5 which measures the pressure drop between the top and bottom of each tray. This provides an indirect measurement of lactide viscosity and conversion which can be used for process control of the thermal cracking operation.

The liquid bottoms in the cracker, which consists mainly of heavy oligomers and complexes, is cooled by a series of cooling coils (A-6) within the bottom of the cracking vessel to a temperature below about 190° C. and the cooled liquid is removed from the cracker via line 27 at a rate such that the average residence time of the heavy ends within the cracking unit is less than about 45 minutes and preferably less than 20 minutes. The heavy ends are removed from the process through line 29 or they are recycled via line 27 to the hydrolysis unit 500 and/or to one of the dehydrator stages 200 and 600 via lines 31 and 33 respectively. Materials recycled to hydrolysis unit 500 are passed via line 35 to scrubber 1400 from which the scrubbed hydrolysate is fed via line 37 either via line 39 to the first dehydrator stage 100 or removed from the process via line 41 to storage vessel 1500.

Figure 1B:
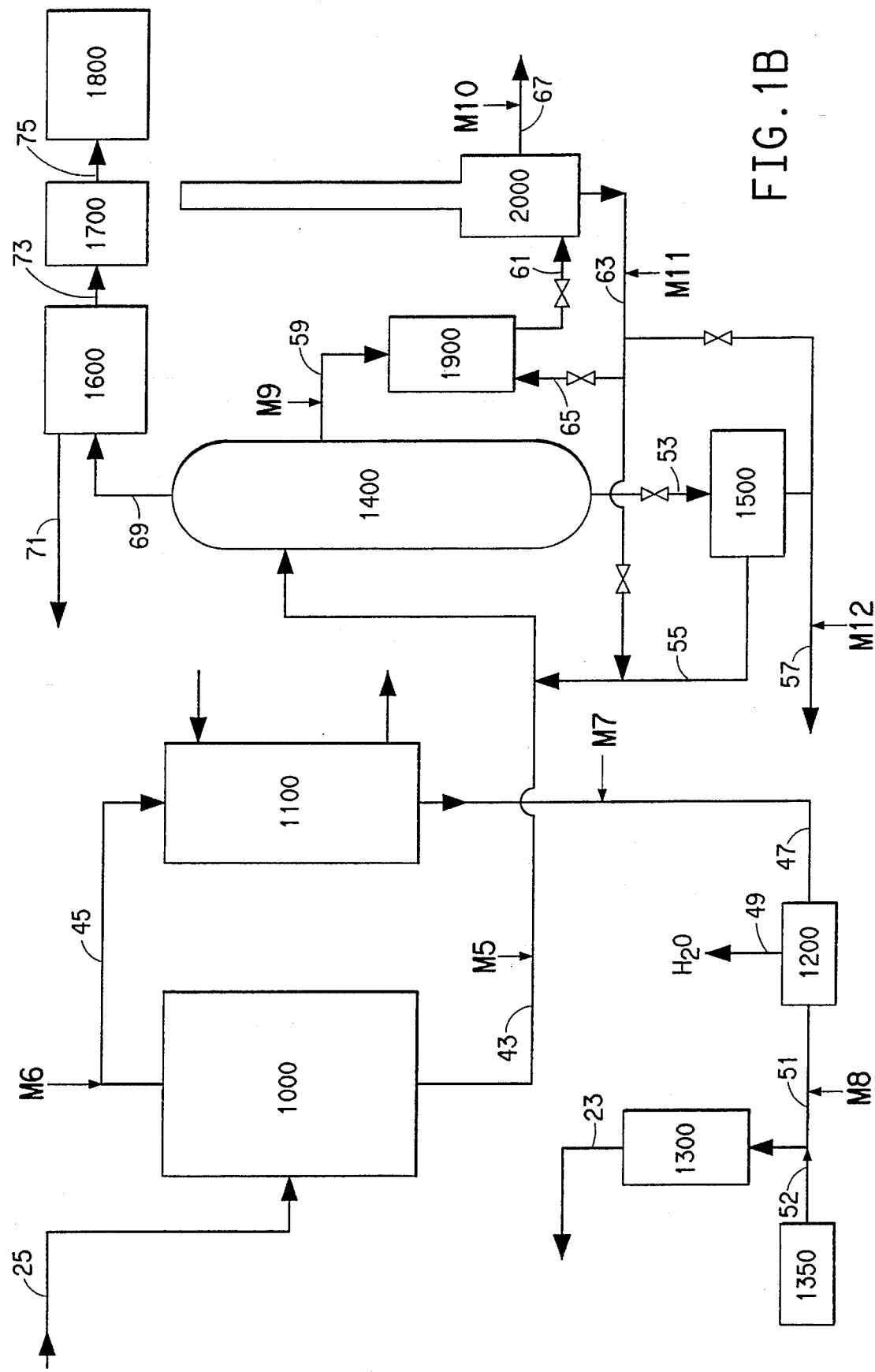

With reference to FIG. 1b, the cracking unit overhead vapor is fed through line 25 to condensor 1000 in which the non-condensable components such as nitrogen, carbon monoxide, carbon dioxide, lactic acid, light decomposition products and water are separated from entrained lactide. The temperature and pressure of condensor 1000 are carefully controlled to maximize the condensation of lactide and minimize the condensation of water vapor.

Non-condensables from condensor 1000 are passed via line 5 to scrubber 1100 in which they are scrubbed with lactic acid to remove residual amounts of liquids in the stream. Scrubbed non-condensables, which comprise mainly nitrogen gas and small amounts of water vapor, are fed via line 47 to dryer 1200 in which water is removed from the nitrogen gas via line 9. The dry nitrogen gas is then fed via line 51 to heater 1300 in which the dry gas is heated to 150°–250° C. and recycled via line 23 to the oligomer cracking vessel 900. Makeup nitrogen gas is supplied to the process from nitrogen storage vessel 1350 via line 52 from which it is mixed with recycled nitrogen gas in line 51.

The condensate from condensor 1000, which is comprised of lactide and minor amounts of heavy oligomers and intermediate lactic acids, is removed from the condensor via line 43 and fed to vacuum distillation column 1400. Optionally, liquid heavy ends from the distillation operation may be admixed with the condensate feed to the distillation column 1400. Distillation column 1400 is preferably a packed column in which light ends are taken overhead, concentrated lactide is removed as a liquid side stream and liquid heavy ends are removed as bottoms to vacuum flashing unit 1500.

As described above, the liquid heavy ends, which are comprised largely of heavy unreacted oligomers and small amounts of partially formed polymers, are heated and subjected to vacuum in order to flash off lighter oligomers and other residual materials. The vacuum flashing overhead from unit 1500 is then passed through line 55 and admixed with lactide feed to distillation column 1400. The residual heavy ends from the vacuum flashing unit are then recycled via lines 57 and 58 to hydrolysis unit 500, and/or dehydrator units 200 and 600 via line 60 and 62 respectively. Residual heavy ends can be removed from the process through line 64.

The concentrated lactide sidestream is removed from distillation column 1400 through line 59 to lactide heater 1900 and then through line 61 to melt crystallization unit 2000 in which the lactide is pumped to the top of the unit and flows down in a thin film which cools and forms purified crystals of lactide. The melt crystallization operation can consist of a single such unit or it can consist of two or more units arranged for either parallel or series operation. Uncrystallized lactide residue flows to the bottom of the unit and is removed from the crystallizer via line 63. Crystallizer bottoms (uncrystallized residue) can therefore be accumulated and recycled to the crystallizer unit by itself or it can be recycled via line 65 in admixture with concentrated lactide feed in heater 1900. Alternatively, the crystallizer bottoms can be removed through line 57 and recycled to hydrolysis unit 500 and/or the dehydration units 200 and 600.

Purified lactide is collected by melting the crystals accumulated on the crystallizer walls and pumping the molten lactide through line 67 to storage or directly to polymerization.

The vapor overhead from the vacuum distillation column 1400, which contains lactic acid, water and small amounts of entrained lactide, is passed through line 69 to condensor 1500 in which the noncondensables are removed through line 73 to cold trap 1700 and thence through line 75 to vacuum pump 1800. The condensed liquid from condensor 1500 is recycled through line 71 to either the hydrolysis unit 500 or to one of the dehydration stages 200 and 600.

In both FIGS. 1a and 1b of the Drawing a number of feasible locations for measuring composition and properties of materials at various stages of the process have been indicated. These locations, which have been labeled M1 through M12, can be used to monitor and/or control process variables. A partial list of such control and/or measurement points is as follows:

| | |
|---|---|
| M1 | (oligomer feed) color, oligomer chain length, catalyst concentration; |
| M2 | (cracker heavy ends) color, chain length, metal content, catalyst concentration; |
| M3 | (cracker vapor) acidity potential, lactide optical purity, entrained catalyst; |
| M3 | (cracker vapor) acidity potential, lactide optical purity, entrained catalyst; |
| M4 | (hydrolysate) lactide optical purity, color, water content, metal content; |
| M5 | (lactide feed) color, water content; |
| M6 | (condenser overhead) water content, gas composition, lactide content; |
| M7 | (scrubbed gas) gas composition, lactide content; |
| M8 | (dried nitrogen) nitrogen flow and purity; |
| M9 | (concentrated lactide) lactide flow volume, acidity potential, optical purity, color; |
| M10 | (purified lactide) acidity potential, optical purity, color; content; and |
| M11 | (crystallizer bottoms) acidity potential, optical purity, polymer content; and |
| M12 | (crystallizer and/or distillation bottoms) color, optical purity, polymer content. |

Test Procedures

Color Measurement: Color measurements of both liquids and solids were carried out using a Minolta Chroma Meter CR-131 manufactured by Minolta Camera Co., Ltd., Osaka, Japan. Color characteristics were indicated using L*a*b* color notation.

Lactide Acidity: Lactide (L) acidity is measured by titration of lactide dissolved in methylene-dichloride ($CH_2Cl_2$) with standardized sodium methoxide (NaMeO) in anhydrous methanol using phenolphthalein indicator. Acidity is calculated as follows:

$$\text{Acidity (meq/kg)} = (1/gL)(mL \text{ titrant} - blank)(\text{molarity factor}).$$

Lactide Isomer Analysis: Lactide isomers are measured by high pressure liquid chromatography (HPLC) in a column with Chiracel® OC packing using 70/30 (wt.) hexane/ethanol as the mobile phase. Lactide samples are dissolved in t-butylmethyl ether and filtered through 0.45 micrometer syringe filter before loading. A 0.5 µL injection is used for each sample and 25 minutes analysis time is allowed. The UV detector is set at 220 nm. Typical retention times for lactide isomers are as follows:

| | |
|---|---|
| L | 14.5 minutes. |
| D | 16.6 minutes |
| Meso | 17.9 minutes. |

Chiracel® is a registered trademark of Diacel Chemical Industries, Tokyo, Japan for tris(3,5-dimethyl-phenylcarbamate) of cellulose and amylose packing.

Metals Analysis: Analyses of metals in the products of the invention were carried out by optical emission spectroscopy, on-line X-ray fluorescence of inductively-coupled plasma techniques.

Oligomer Chain Length: Oligomer is dissolved in 80/20 (wt.) anhydrous methylene-dichloride/methanol and titrated with 0.1M NaMeO in anhydrous MeOH using phenolphthalein indicator as follows:

$$\text{Avg. M.W.} = (10,000/mL\ 0.M \text{ titrant}) \times [1/\text{oligomer wt.}(g)] \quad (1)$$

$$\text{Chain length } (n) = [(\text{Avg. M. Wt.} - 90)/72] + 1 \quad (2)$$

Optical Purity: Optical rotation is a function of optical purity. Therefore optical purity was determined by measuring the optical rotation of various liquids using a SR-6 polarimeter made by PolyScience, a Division of Preston Industries, Inc., Chicago, Ill.

Partial Polymerization: Solution cloudiness is a quantitative measure of lactide partial polymerization using a Hoch Chemical turbidimeter No. 18900 (Hoch Chemical, Ames, Iowa).

$Sn^{II}$ Analysis: Divalent tin is measured by redox titration with $Ce^{IV}$ using phenanthralene ferrous sulfate as a colorimetric indicator. The titration is preferably carried out under nitrogen gas. The material to be analyzed is dissolved in water/acetone. A 0.025M titrant solution of cerium (IV) sulfate in 2N sulfuric acid was prepared. A 0.05M ferrous ammonium sulfate solution was used to standardize the cerium sulfate. Ten mL of the ferrous ammonium sulfate solution was placed in a beaker with 25 mL of methanol and 25 mL of acetone. Three drops of 0.025M 1,10 phenanthralene ferrous sulfate was added as an indicator. The standard was titrated with the cerium until a light lemon yellow endpoint was reached. The cerium molarity was calculated from the average of three titrations as follows:

$$\text{Molarity} = (10\ mL \times 0.05\ mole/L)/mL \text{ of Ce(IV) titer}$$

Weighed 2 g samples of Sn(II)-containing unknowns were dissolved in 4S mL of acetone and 5 mL of $H_2O$ was added to promote stable endpoint formation. Three drops of 0.025M 1,10 phenanthralene ferrous sulfate indicator were added and the mixture titrated with cerium sulfate until a light lemon yellow endpoint was reached. The percent Sn(II) in the sample was calculated by the following equation:

% wt. Sn(II)=Molarity of Ce×(mL titer−blank)×5.9345 Sn(II)/ Sample weight in grams Water Analysis: The moisture (water) content of materials is measured by titration of water with iodine in the presence of $SO_2$ in a suitable base. In particular, a 10% wt. solution of lactide in methanol/water is prepared under dry nitrogen gas. The titration is carried out using a Karl Fischer Titrator, DL18, made by Mettier Instrumente AG, Griefensee, SU. The water content of the solution is then compared with the known water content of HPLC-grade $CHCl_3$.

EXAMPLES

Example 1

This example illustrates the effect of various operating variables during the dehydration step(s) of the invention.

In each of a series of four test runs, eight liters of commercial 88% wt. aqueous lactic acid (98% L) were placed in a sealed stirred tank reactor. The liquid was well agitated by means of a centrally mounted impeller operating at 850–950 r.p.m. Heat was controllably added to the agitated liquid by means of two wall mounted 840 watt electric heaters which maintained the heat input so that the temperature difference between the wall and the bulk liquid did not exceed 15° C. and the liquid temperature did not exceed 190° C.

To speed up water removal, the reaction system was operated a reduced pressure of 50–200 mm Hg. To lessen loss of light lactic acid species, the overhead vapor was passed through a 5 tray column in which the lactic acid species were condensed and refluxed back into the bulk lactic acid liquid. Each of the test runs exhibited similar water removal rates. (See FIG. 2a.) In particular, water removal rates were rapid during the first 2.5–3 hours of operation, after which the water removal rate slowed down considerably. Maximum water removal was obtained at about 4 hours.

Figure 2B:
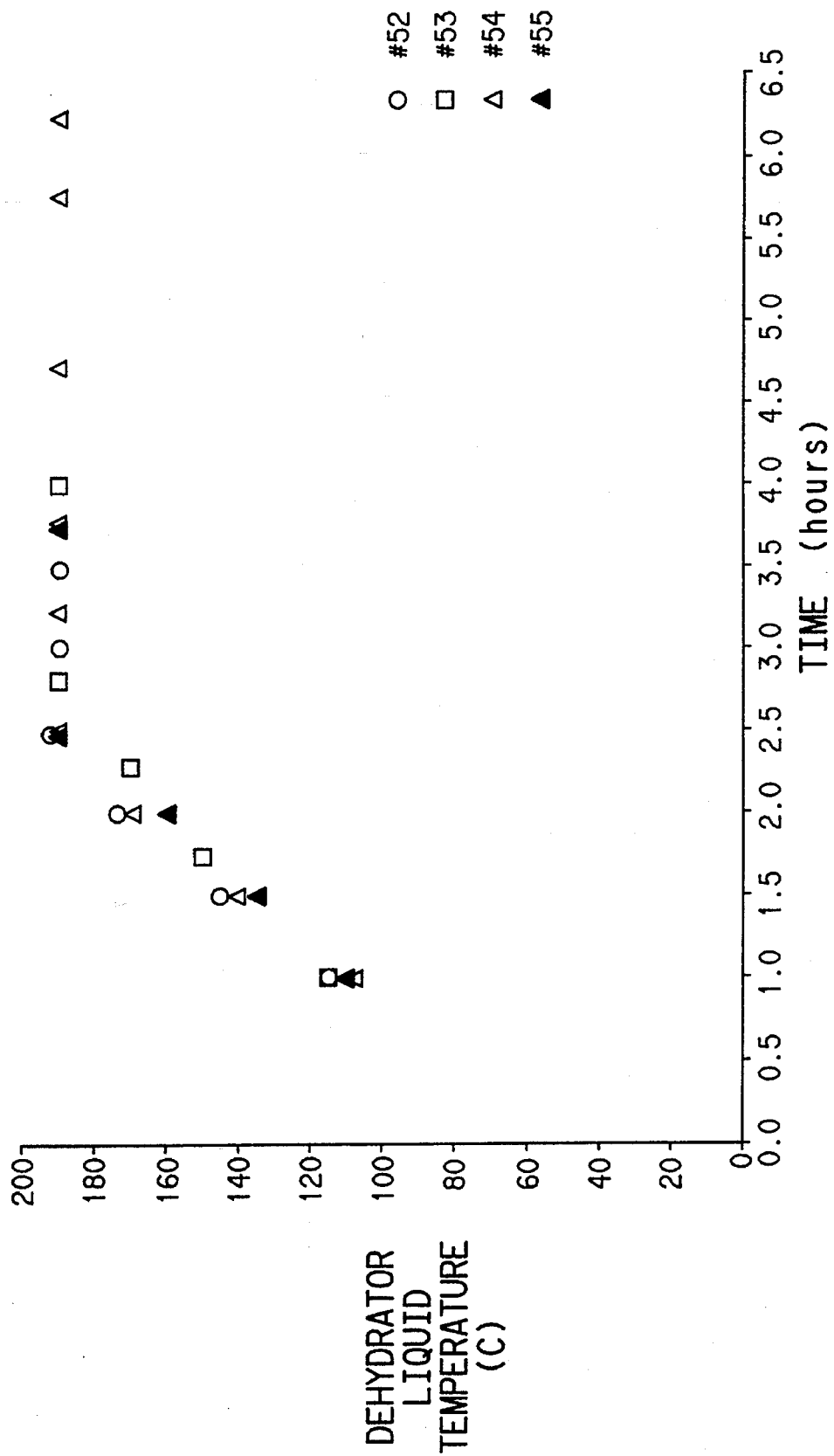
FIGS. 2a, b and c, FIGS. 3a and b and FIG. 4 are graphical correlations of various operating variables associated with the dehydration step of the invention.

FIG. 2b from the same tour test runs shows that the maximum temperature of 190° C. was reached in about 2.5 hours, after which the temperature remained substantially constant throughout the remainder of the runs (3–6 hours). In this regard, an upper limit on temperature is required to avoid decomposition and racemization problems as well as premature formation of lactide.

Figure 2C:
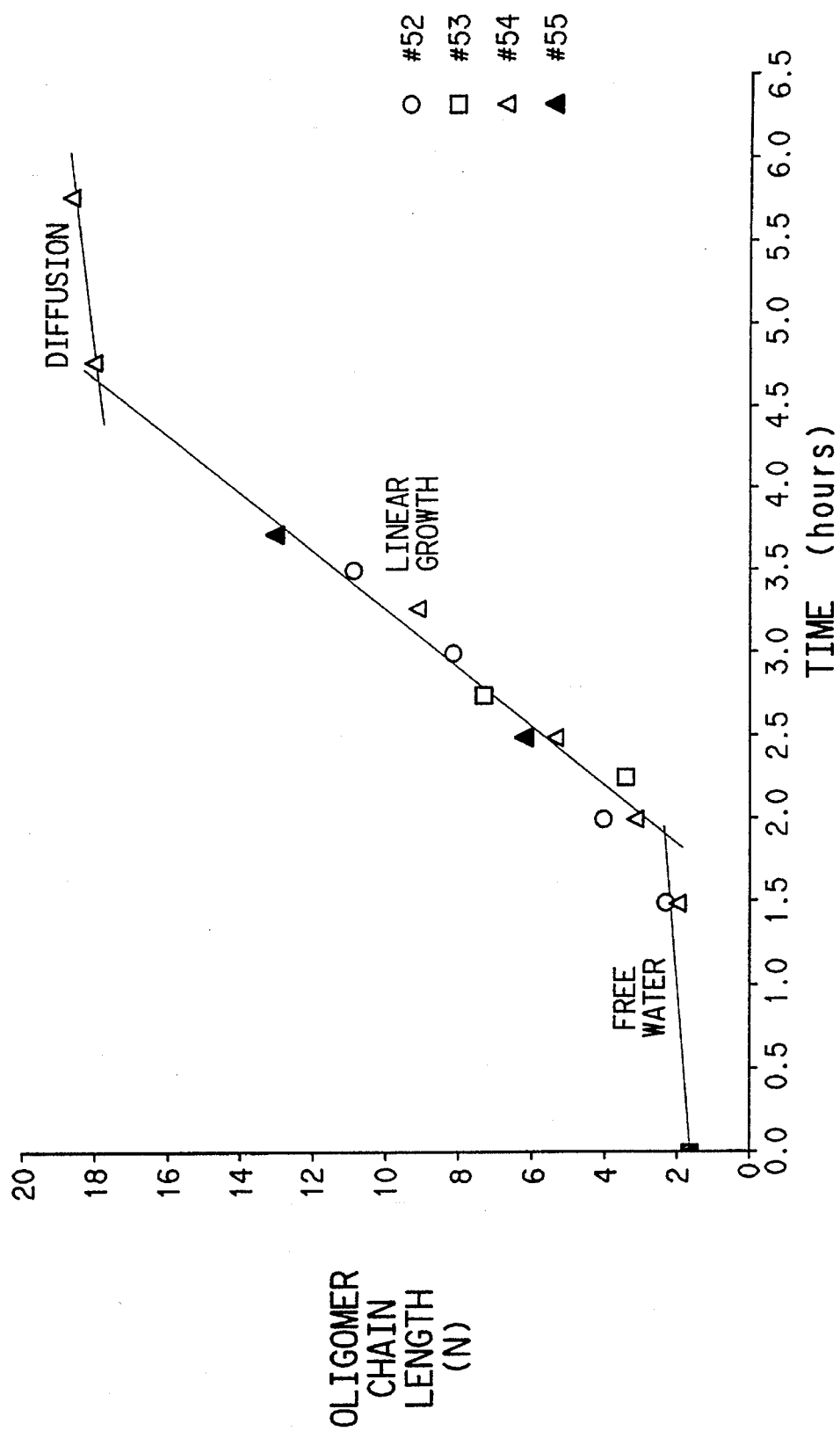

FIG. 2c from the same tour test runs is a graphical correlation of oligomer chain length as a function of time during the tests. These data show that during the first 2 hours, substantially only free water was removed from the reaction system and the average chain length of the oligomers (n) was only 2. When the process of the invention is carried out continuously, fresh lactic acid feed should be introduced into this stage.

From 2 to 4.5 hours into the run, chain growth took place until n was about 20. Such high chain length oligomers are very viscous. After 4.5 hours, very little chain further growth took place because of the high viscosity and thus low diffusivity of such heavy oligomers. It is clear that fresh lactic acid feed should not be introduced into this stage since the free water therein would back-hydrolyze the oligomer chains.

After about 4.5 hours, the actual amount of water remaining in the system was very small and the viscosity of the oligomers was quite high. At this point it is important to minimize further exposure to high temperature and thus to reduce degradation, racemization and premature lactide formation.

Example 2

Upon recognizing the important effect of viscosity in limiting residual water diffusion from the oligomers, dehydration tests were performed using equipment in which the diffusive surface of the oligomers was enhanced in order to facilitate further diffusion of water from the oligomers.

Figure 3A:
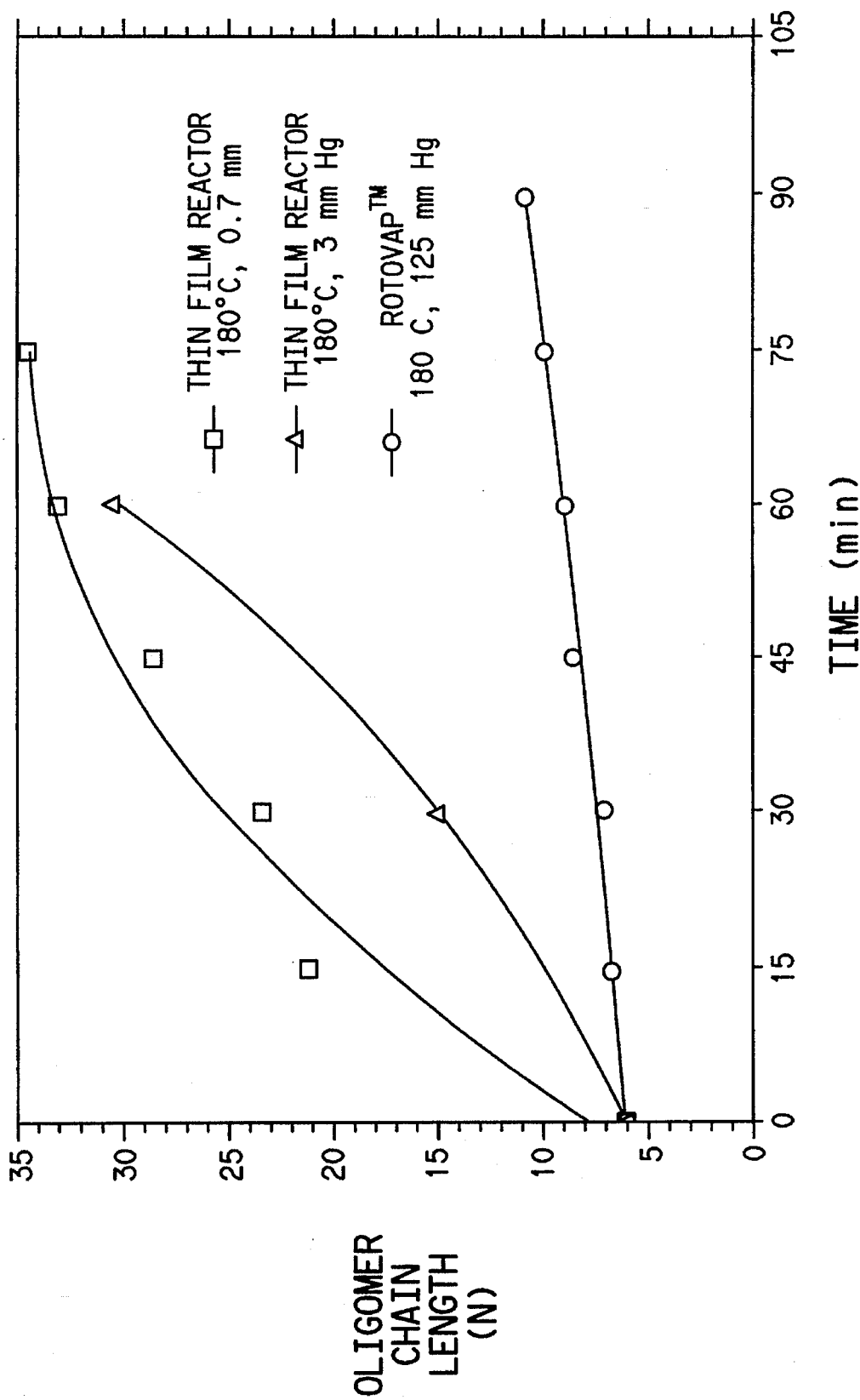
Figure 3B:
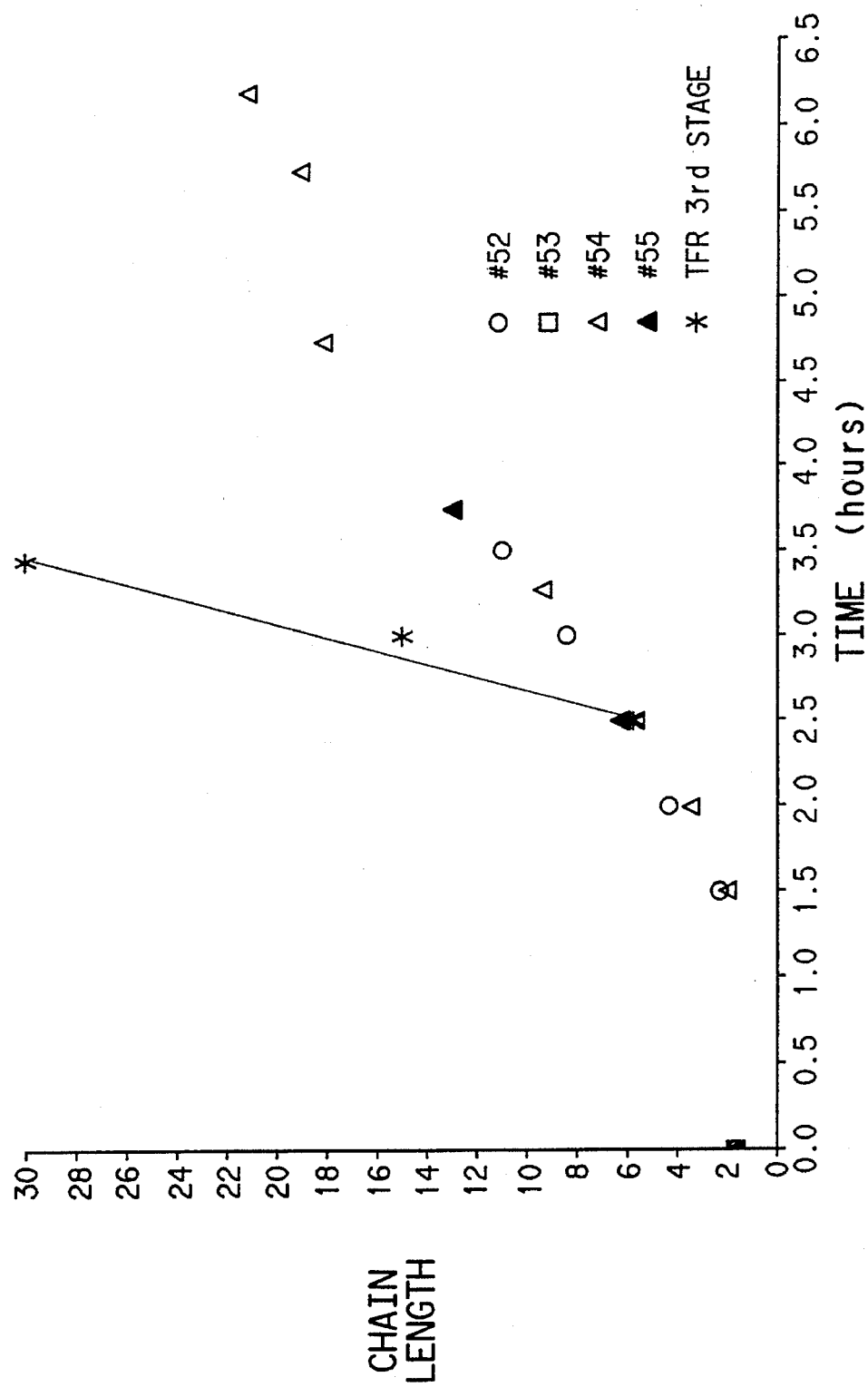

In particular, separate quantities of oligomer (n=6) were dehydrated at 180° C. under vacuum (0.7 mm Hg and 3 mm Hg) in a twin screw devolatilizer and an additional quantity of the same oligomer was dehydrated in a rotary flask evaporator (Rotovap™ flask evaporator) at 125 mm Hg. The former apparatus creates a very thin wiped film of oligomer, while the latter apparatus increases the diffusion area of the oligomer by centrifugally swirling the oligomer around the inner surface of the flask. Both devices enhance the diffusive area of the oligomer, but the enhancement in the devolatilizer is substantially higher. FIG. 3 is a graphical presentation of the oligomer chain length as a function of time during these tests.

The data in FIG. 3 show that the rate of chain length growth in the extruder thin film reactor was several times faster than in the rotary flask evaporator. For example, after only 15 minutes in the extruder, the value of n had reached 10–17. On the other hand, the oligomer dehydrated in the rotary flask evaporator reached n=11 only after 90 minutes. These data show very clearly the advantage of surface enhancement to reduce the time needed to obtain a given degree of oligomerization and thus considerably to reduce thermal exposure of the oligomer.

It is interesting to note that the diffusion area enhancement combined with vacuum operation of the dehydrator enabled very high molecular weight oligomers (n=30–35) to be formed quite easily.

When the data from the above-described 3 mm Hg run were superimposed on the data from FIG. 2c, the advantage of enhanced diffusive surface was shown more clearly still. For example, oligomer in which n=18 was obtained in only about 0.5 hour of dehydration as compared with over 2.5 hours being required to reach the same level of oligomerization without surface enhancement.

Example 3

A further series of experimental dehydration runs was carried out at 0.7 mm Hg using the above-described equipment in which the temperature was varied from 180° C. to 200° C. FIG. 4 shows the results of this series of tests.

The highest molecular weight oligomers (n=30–35) were obtained at 190° C., while operation at 200° C. yielded oligomers in which the value of n was only 20–25. Operation at 180° C. under these conditions yielded oligomers in which n was higher than 30 after one hour's operation. These data, of course, show clearly the effect of temperature on oligomer molecular weight due to thermal decomposition, principally depolymerization and lactide formation. Though still lower operating pressures are technically feasible and would result in higher n values at temperatures above 190° C., such operating pressures are not at this time economical for commercial scale operations.

Example 4

The various process steps which are involved in the manufacture of purified lactide can be difficult to control because of many side reactions which occur because of the presence of various impurities. It has been found that the generation of color and its measurement is a sensitive indicator by which the effect of such impurities can be observed. Accordingly, a series of tests was conducted to determine the effect of several materials on lactide color. The tests were conducted on the materials glass, Hastelloy, AL6XN, titanium, zirconium and 304 SS. Additional tests were also conducted to observe the effects of time-temperature exposure and the effects of catalyst contained in the lactide.

In these tests a commercially available heat stable lactic acid is placed in a sealable container. A carefully cleaned piece of the material being tested is then half-immersed in the lactic acid, the head space is blanketed with nitrogen and the container sealed. The sealed container is then maintained at 120° C. and changes in the color of the lactic are observed over the course of time. In addition the material is examined by optical emission spectroscopy to observe corrosion incurred during the submersion.

Results of the corrosion tests are given in Table I below:

TABLE 1

Corrosion of Materials in Lactic Acid

| Material | % Fe | Corrosion Products, ppm | | |
|---|---|---|---|---|
| | | Fe | Cr | Ni |
| Glass | 0 | 12 | 1 | 1 |
| Hastelloy | 4 | 12 | 4 | 12 |
| AL6XN | 48 | 17 | 2 | 3 |
| 304 SS | 75 | 160 | 55 | 18 |

These data show the distinctly greater susceptibility to corrosion of high ferrous materials in the presence of lactic acid.

Example 5

A series of laboratory experiments was conducted to observe the effect of iron in materials of construction on the degradation of lactide in contact with such materials. In this series of tests, high quality L-lactide was placed in a series of carefully dried glass containers. Into these containers were placed clean pieces of 316SS, AL6XN, Hastelloy and glass and the containers were inerted with nitrogen and sealed. The sealed containers were then heated at 130° C. for 72 hours. Upon completion of the test period, the samples were analyzed by HPLC to determine the loss of lactide from each container and the color of the lactide was measured in the manner described hereinabove. The following data from these experiments show that the loss of lactide was related directly to the amount of iron contained in the material of construction:

TABLE 2

Effect of Construction Materials on Lactide Color

| Material | Iron Content (% wt.) | Lactide Loss (% wt.) |
|---|---|---|
| Glass | None | 0.0 |
| Hastelloy | 4 | 1.6 |
| AL6XN | 48 | 5.9 |
| 316SS | 100 | 13.0 |

Figure 5:
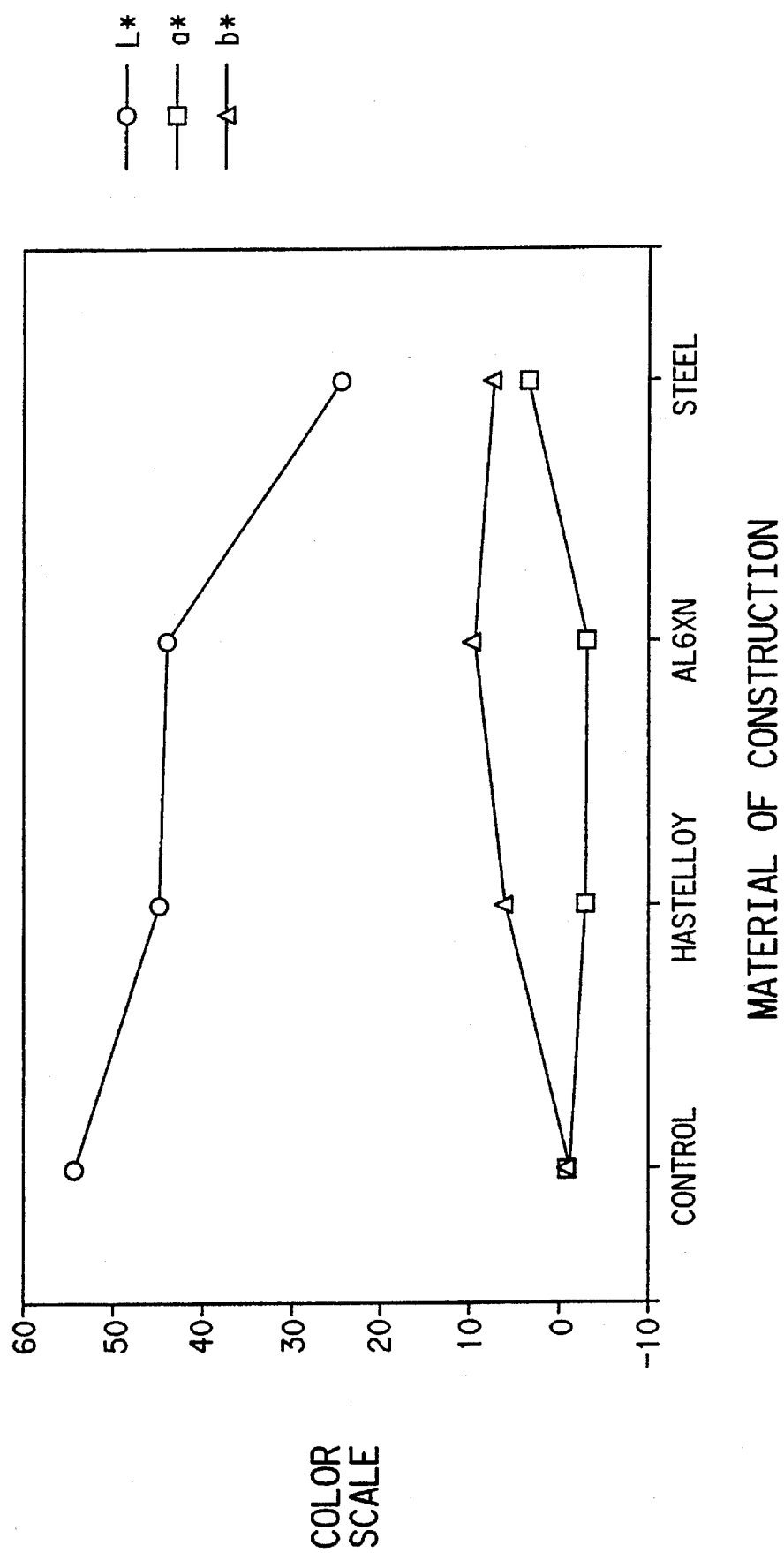
FIG. 5 is a graphical correlation of the effect of construction materials on lactide color.

L*a*b examination of the discolored lactide (FIG. 5) shows that the formation of dark color (L) was a direct function of the iron content of the material in which the lactide was in contact.

Example 6

A lactic acid oligomer having a molecular weight of 738 (n=10) was admixed with 1.5% by weight high purity tin octoate and fed at a nominal rate of 35 g/minute to a single sieve tray column. The tray was made of Hastelloy C and had an adjustible weir set at 0.75 inch height.

The sieve tray was 8 inches in diameter, 0.125 inch thick and perforated with 216 evenly spaced 0.067 inch holes. Inlet feed temperature was held at 190° C. maximum in order to lessen catalyst degradation, color formation, racemization of oligomer and lactide produced therefrom. Actual liquid temperatures on the tray were controlled to 210°–215° C. Heated nitrogen gas (215° C.) was passed upward through the sieve tray at a rate of 140 standard cubic feet per hour (SCFH) to strip out the formed lactide very quickly, thus reducing the potential for decomposition, partial polymerization and racemization of the reactants and products therefrom. Data from this experiment are given in Table 3 below:

TABLE 3

Effect of Time and Temperature on Reaction and Racemization

| Time (min.) | Feed Rate (g/hour) | Acidity (meq/kg) | Total Lactide (% w) | Isomer Distribution (% w) | | |
|---|---|---|---|---|---|---|
| | | | | L | D | Meso |
| 15 | 450 | 907 | 71.6 | 95.4 | — | 4.6 |
| 75 | 386 | 907 | 88.4 | 92.4 | — | 7.6 |
| 135 | 322 | 802 | 85.1 | 87.2 | 1.3 | 11.5 |
| 165 | 210 | 256 | 93.4 | 78.3 | 4.1 | 17.5 |

The above data show a gradual decline in the rate of formation of L lactide coupled with a gradual increase in meso lactide formation as a function of time resulting from degradation of the oligomer/catalyst mixture. In particular, It is believed that this phenomenon is due to the oxidation of $Sn^{II}$ to $Sn^{IV}$ with a concomitant loss of electrons which reduce and thus degrade the lactide. These data confirm the desirability of minimizing time/temperature exposure of catalyst and oligomer in the cracking step.

Example 7

Figure 6:
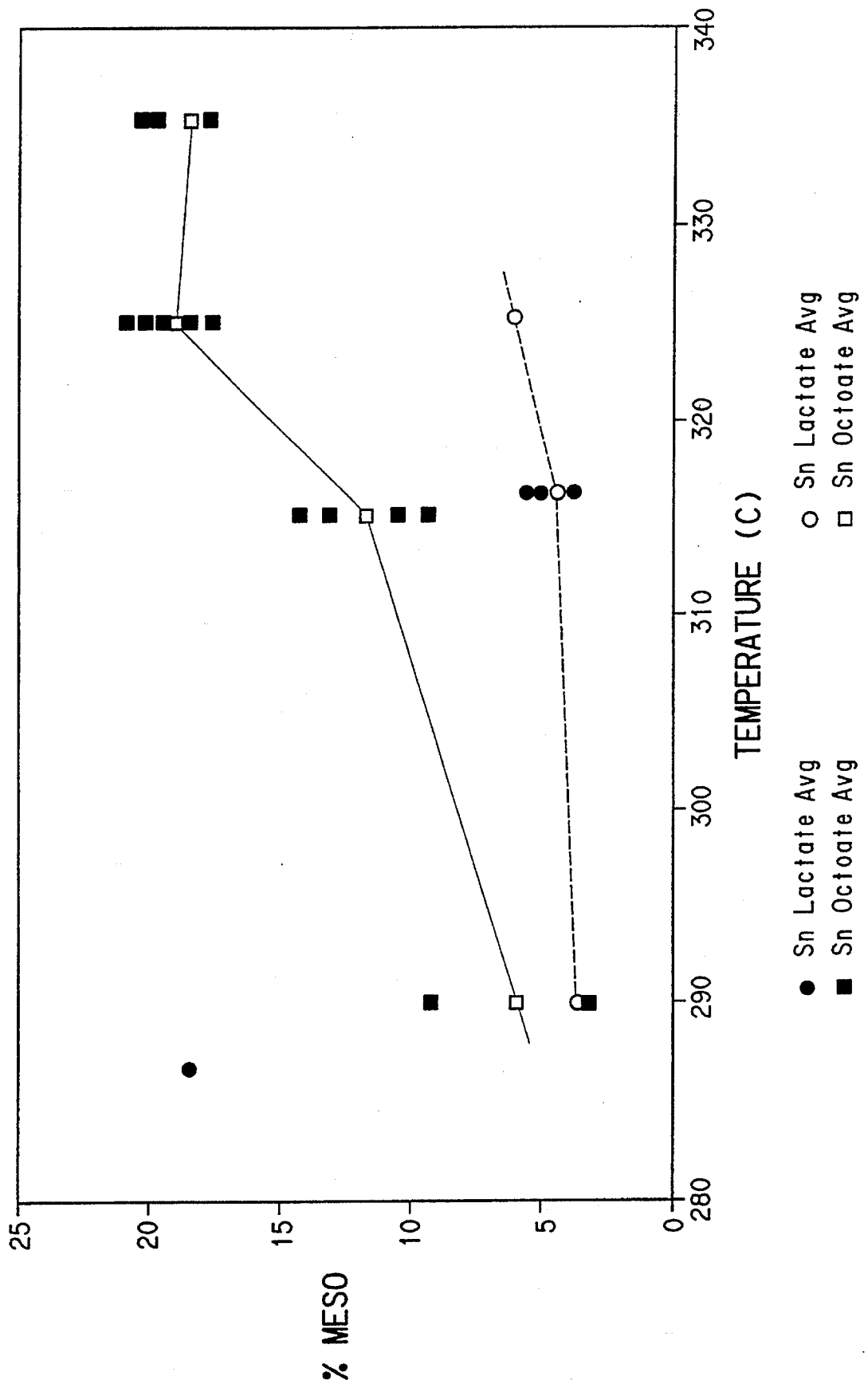
FIG. 6 is a graphical correlation of the concentration of meso enantiomer as a function of temperature.

To observe the effect of alkali metal contamination on lactide formation by depolymerization, runs were carried out comparing commercially available $Sn^{II}$ octoate catalyst containing 3,000 ppm by weight, sodium contamination with a tin octoate catalyst which contained only 50 ppm by weight sodium contamination. Both materials were used at a concentration of 0.5% by weight to depolymerize oligomer having a molecular weight of 1460 (n=19) at 290°–335° C. in a thin film reactor operated at a pressure of 10 mm Hg and 6 seconds residence time. The data from this test are given in FIG. 6 which shows that the high-sodium catalyst yielded substantially higher amounts of undesirable concentrations of the meso enantiomer even at the lower temperatures and the meso content rose substantially to over 20% by weight as the reaction temperature was raised to a level of 330° C. On the other hand, the low-sodium catalyst yielded only about 6% weight meso lactide at 330° C. These data show clearly the desirability of using catalysts having low alkali metal content and minimizing the depolymerization temperature.

Example 8

In this example, a series of three depolymerization catalysts was used to show further the adverse effect of alkali metal concentration on the racemization of lactide produced thereby. Three antimony catalysts were used—SbNa lactate, SbNH₄lactate and SbOctoate the last of which contained only 50 ppm by weight sodium. These three catalysts were mixed with lactic acid oligomers having a molecular weight of 450 (n=6) and were heated in an inerted small batch flask reactor at 180°–190° C. and the resulting lactide vapors were collected and condensed over a 30 minutes period. The data from these three tests are given in Table 4 below.

TABLE 4

Effect of Alkali Metal Contamination on Meso Lactide Formation

| Catalyst | Total Lactide % wt. | L % wt. | D % wt. | Meso % wt. |
|---|---|---|---|---|
| SbNaLactate | 83.7 | 36.5 | 27.2 | 36.3 |
| SbNH₄Lactate | 78.6 | 89.6 | 1.3 | 9.0 |
| SbOctate | 71.5 | 95.7 | 0.0 | 4.3 |

These data again show the deleterious effect of alkali metal ions, such as sodium, on the racemization of lactide produced by cracking of lactic acid oligomers in the presence of metal catalysts.

Example 9

Using the same type of equipment as in the Example 8, a series of tests was run in which the effect of different anions was observed. In particular, the runs were conducted on lactic acid oligomer having a molecular weight of 450 (n=6) at 180°–190° C. using catalyst concentrations of 0.5% by weight. The resulting lactide vapors were swept from the flask with nitrogen, collected and condensed and the condensate was analyzed. The data from this comparison are given in Table 5 below.

TABLE 5

Effect of Catalyst Anion Volatility on Lactide Production

| Catalyst | % wt. Lactide | % wt. L | % wt. D | % wt. Meso |
|---|---|---|---|---|
| SnCl₂ | 33.1 | 96.2 | 0.0 | 3.6 |
| SnSO₄ | 76.9 | 86.0 | 7.9 | 6.1 |

Analysis of the lactides showed that the one derived by cracking in the presence of the chloride-containing catalyst had a high acid level (2,000 ppm) and the above data show a very low yield of lactide was obtained. Moreover, the product was dark in color and had a high odor level. Meso level was low, probably because of its relatively high instability. However, depolymerization using the sulfate catalyst resulted in more than twice the amount of lactide recovery, the lactide had little odor and was white in color. These data indicate that non-volatile acidic species such as $H_2SO_4$, which remain in the residue, are preferable to more volatile acidic species such as HCl, which remain in the lactide overhead vapor from the cracking operation.

Example 10

A further experiment was carried out in which pure lactide and a small weighed piece of carefully cleaned steel wool were placed in a glass bottle in which the head space was inerted with nitrogen gas and the bottle was sealed. The bottle was then placed in a 120° C. oven for 72 hours, after which the bottle was opened and the steel wool was washed and reweighed.

Surprisingly, reweighing the steel wool revealed that there was no weight loss nor any change in the properties of the steel wool. Thus, there was no corrosion of the steel wool. Nevertheless, the lactide had turned brown and the lactide acidity had increased from 1.5 meq to 166 meq. Analysis by HPLC revealed an 8.7% weight loss in lactide. These data therefore indicate that the loss of lactide was incurred by water generated internally during reaction of the lactide catalyzed by the presence of the iron.

We claim:

1. An integrated process for the manufacture of purified lactide from an aqueous solution containing at least 50% wt. lactic acid comprising the sequential steps:

A. Feeding a solution of crude lactic acid in de-ionized water to a first heated zone in which free water is removed by evaporation and a molten mass of condensation polymer containing lactic acid is formed by condensation polymerization to an extent that the average number of monomer units (n) in the condensation polymer is 2–8;

B. Feeding the molten mass of condensation polymer from step A to at least one further heated zone in which the diffusive surface area of the polymer is increased, the residual lactic acid and condensation polymer are further condensation-polymerized to an extent that n is 8–25 and both free water and bound water are removed by evaporation, steps A and B being carried out within equipment the surfaces of which in contact with the reactants are fabricated from low ferrous materials;

C. Contacting the molten condensation polymer with an alkali metal-free depolymerization catalyst in a cracking zone operated at a liquid temperature no higher than 240° C. and pressure sufficient to effect cracking of the molten condensation polymer with the concomitant formation of (1) a vaporous reaction mixture containing water, lactic acid, lactide and entrained heavy oligomers and (2) molten liquid heavy ends containing heavy oligomers;

D. Removing the vaporous reaction mixture from the cracking zone at a rate such that the average residence time of the lactide vapor within the cracking zone is less than 15 seconds;

E. Condensing the vaporous reaction mixture and vacuum fractionally distilling the condensate therefrom whereby lactic acid, water and minor amounts of lactide are removed as vapor overhead, concentrated lactide is removed as a liquid side stream and the heavy ends are removed as molten liquid; and F. Subjecting the concentrated lactide to melt crystallization by which purified lactide having an Acidity Potential less than 6 meq/kg of lactide is separated from a residual lactide having an acidity potential of at least 30 meq/kg.

2. The process of claim 1 in which steps A–E are carried out continuously.

3. The process of claim 1 in which step B is carried out under vacuum at a temperature no higher than 200° C.

4. The process of claim 1 in which water vapor removed from the condensation polymer in steps A and/or B is scrubbed with hot lactic acid to remove residual amounts of lactic acid contained therein.

5. The process of claim 1 in which steps A and B are carried out in a packed column.

6. The process of claim 4 in which the residual amount of lactic acid removed is recycled to steps A and/or B.

7. The process of claim 1 in which the molten condensation polymer is admixed with heated depolymerization catalyst and the admixture is introduced into the cracking zone.

8. The process of claim 7 in which the polymer-catalyst admixture is comprised of 0.1–5% wt. catalyst and is heated to a temperature of 150°–240° C.

9. The process of claim 8 in which the catalyst is a soluble organic compound of a metal selected from Sn, Sb, La, rare earth metals and mixtures thereof.

10. The process of claim 9 in which the catalyst is comprised of finely divided particles of an insoluble metal-containing material.

11. The process of claim 1 in which the molten condensation polymer is passed through a fixed foraminous bed of depolymerization catalyst contained within the cracking zone.

12. The process of claim 1 in which the cracking step is carried out at about atmospheric pressure and a liquid temperature of at least 200° C.

13. The process of claim 1 in which the cracking step is carried out under vacuum.

14. The process of claim 1 in which nitrogen gas is introduced into the vapor space in the lower end of the cracking zone to effect stripping of the vaporous reaction mixture from the heavy ends.

15. The process of claim 1 in which the molten liquid heavy ends in the bottom of the cracking zone are cooled to a temperature below 190° C. and removed from the cracking zone at a rate such that the residence time of the liquid heavy ends within the cracking zone is less than 15 minutes.

16. The process of claim 1 in which the molten liquid heavy ends from the cracking zone in step C are recycled to step A and/or B.

17. The process of claim 1 in which the cracking zone is comprised of a plurality of spaced perforated trays having controllable heat exchange means for heating liquid contained on the trays and downcomers for transferring liquid between the trays.

18. The process of claim 1 in which fractionation of the condensate in step E is carried out under vacuum.

19. The process of claim 1 in which the lactide residue from step is fed to a heated vacuum zone in which lactide is vaporized from the residue, condensed and recycled to step A, B, C or E.

20. A process for making a concentrated stream of lactide from lactic acid oligomers comprising the sequential steps:

A. Contacting molten lactic acid oligomers in which the average number of monomer units is 8–25 with an alkali metal-free depolymerization catalyst in a cracking zone operated at a temperature no higher than 240° C. and pressure sufficient to effect cracking of the molten oligomers with the concomitant formation of (1) a vaporous reaction mixture containing water, lactic acid, lactide and entrained heavy oligomers and (2) molten cracker bottoms containing heavy oligomers;

B. Removing the vaporous reaction mixture from the cracking zone at a rate such that the average residence time of the lactide vapor within the cracking zone is less than 15 seconds;

C. Condensing the vaporous reaction mixture and fractionally distilling the condensate therefrom whereby lactic acid, water and minor amounts of lactide are removed as vapor overhead, concentrated lactide is removed as a liquid sidestream and the condensate heavy ends are removed as molten liquid;

D. Cooling the molten cracker bottoms to below 190° C. and removing them from the cracking zone at a rate such that the average residence time of the molten cracker bottoms in the cracking zone is less than 15 minutes; and E. Subjecting the cooled molten cracker bottoms to either dehydration or hydrolysis followed by dehydration and recycling the resultant dehydrate to the cracking zone.

21. The process of claim 20 in which the concentrated lactide from Step C is subjected to melt crystallization by which purified lactide having an acidity potential less than 6 mek/kg of lactide is separated from a residual lactide having an Acidity Potential of at least 30 meq/kg.

22. A method for making oligomers of lactic acid which are suitable for depolymerization to form lactide comprising the sequential steps:

A. Feeding a solution of crude lactic acid in de-ionized water to a first heated zone in which free water is removed by evaporation and a molten mass of condensation polymer containing lactic acid is formed by condensation polymerization to an extent that the average number of monomer units (n) in the condensation polymer is 2–4; and B. Feeding the molten mass of condensation polymer from step A to at least one further heated zone in which the diffusive surface area of the polymer is increased, the residual lactic acid and condensation polymer are further condensation-polymerized to an extent that n is 8–25 and both free water and bound water are removed by evaporation, steps A and B being carried out within equipment the surfaces of which in contact with the reactants are fabricated from low ferrous materials.

23. A method for making poly(lactic acid) comprising:

A. a ring-opening catalyst selected from the group consisting of metal oxides, carbonates and carboxylates of $Sn^{II}$, $Sb^{III}$, $Zn^{II}$ and $Bi^{III}$, compounds of trivalent lanthanum and rare earth metals admixed with purified lactide made by the process of claim 1 or claim 21; and B. heating the admixture under pressure to a temperature of 100°–200° C. to effect formation of poly(lactic acid) by ring-opening polymerization of the lactide.

* * * * *